US006087188A

United States Patent [19]
Johansen et al.

[11] Patent Number: 6,087,188
[45] Date of Patent: *Jul. 11, 2000

[54] TWO-SITE IMMUNOASSAY FOR AN ANTIBODY WITH CHEMILUMINESCENT LABEL AND BIOTIN BOUND LIGAND

[75] Inventors: Niels Johansen, Allerød; Hans-Henrik Ipsen, Hillerød, both of Denmark

[73] Assignee: ALK A/S, Horsholm, Denmark

[*] Notice: This patent issued on a continued prosecution application filed under 37 CFR 1.53(d), and is subject to the twenty year patent term provisions of 35 U.S.C. 154(a)(2).

[21] Appl. No.: 08/879,988

[22] Filed: Jun. 20, 1997

Related U.S. Application Data

[63] Continuation of application No. 08/436,188, May 10, 1995, abandoned.

[30] Foreign Application Priority Data

Nov. 13, 1992 [DK] Denmark .................. 1379/92

[51] Int. Cl.$^7$ .................. G01N 33/553
[52] U.S. Cl. .................. 436/526; 435/7.1; 435/7.5; 435/7.92; 435/7.95; 435/174; 435/181; 435/971; 436/507; 436/512; 436/513; 436/518; 436/523; 436/524; 436/525; 436/532; 436/538; 436/547; 436/548; 436/811; 436/821; 436/824
[58] Field of Search .................. 435/7.1, 7.5, 7.92–7.95, 435/174, 181, 971; 436/507, 512, 513, 518, 523, 524, 525, 526, 532, 538, 547, 548, 811, 821, 824

[56] References Cited

U.S. PATENT DOCUMENTS

| 4,163,779 | 8/1979 | Harte et al. .................. 424/1 |
| 4,228,237 | 10/1980 | Hevey et al. .................. 435/7 |
| 4,444,879 | 4/1984 | Foster et al. .................. 435/7 |
| 4,496,654 | 1/1985 | Katz et al. .................. 435/7 |
| 4,535,057 | 8/1985 | Dreesman et al. . |
| 4,745,181 | 5/1988 | Law et al. . |
| 4,935,339 | 6/1990 | Zahradnik . |
| 4,946,958 | 8/1990 | Campbell et al. .................. 546/104 |
| 5,028,524 | 7/1991 | Fujisawa et al. . |
| 5,210,017 | 5/1993 | Carlsson et al. .................. 435/7.8 |
| 5,395,938 | 3/1995 | Ramakrishnan. .................. 546/104 |

FOREIGN PATENT DOCUMENTS

| 201079 | 11/1986 | European Pat. Off. . |
| 0 425 218 A2 | 10/1990 | European Pat. Off. . |
| 55-92693 | 7/1980 | Japan . |
| 88/05538 | 7/1988 | WIPO . |
| 89/10565 | 11/1989 | WIPO . |
| 90/08957 | 8/1990 | WIPO . |

OTHER PUBLICATIONS

"Magnetic Solid–Phase Enzyme Immunoassay for the Quantitation of Antigens and Antibodies: Application to Human Immunoglobulin E"; *Methods In Enzymology*; vol. 73; 1981; pp. 471–482.

"Avidin–Biotin Coupling as a General Method for Preparing Enzyme–Based Fiber–Optic Sensors"; *Analytical Chemistry*; May 15, 1989; vol. 61, No. 10; pp. 1069–1072.

"Improved Immunoglobulin M Serodiagnosis in Lyme Boreoliosis by Using a μ–Capture Enzyme–Linked Immunosorbent Assay with Biotinylated *Borrelia burgdorferi* Flagella"; *Journal of Clinical Microbiology*; Jan.1991; vol. 29, No. 1; pp. 166–173.

(List continued on next page.)

*Primary Examiner*—James C. Housel
*Assistant Examiner*—Bao-Thuy L. Nguyen
*Attorney, Agent, or Firm*—Watov & Kipnes, P.C.

[57] ABSTRACT

A method of detecting an antibody in a sample using a labelling compound and comprising the steps of mixing a ligand antigen, antibody or hapten bound to biotin with the sample; an antibody directed against the antibody to be detected bound to paramagnetic particles; and a chemiluminescent acridinium compound bound to avidin or streptavidin to form a solid phase complex; separating the solid phase from the liquid phase; and analyzing the separated solid phase for the presence of chemiluminescent complex.

18 Claims, 8 Drawing Sheets

OTHER PUBLICATIONS

"The Use of Avidin–Biotin Interaction in Immunoenzymatic Techniques"; *The Journal of Histochemistry and Cytochemistry*; vol. 27, No. 8; pp. 1131–1139; 1979.

"Avidin–Biotin System in Enzyme Immunoassays"; *Methods in Enzymology*; 1990, vol. 184; pp. 469–481.

"Biotin–labelled antigen screening test for toxoplasma IgM antibody"; *J. Clin. Pathol.*; 1989; 42:206–209.

"Capture assay for specific IgE An improved quantitative method"; *Journal of Immumological Methods*; 157(1993) 65–72.

"Measurement of antigen–specific mouse IgE by a fluorometric reverse (IgE–capture) ELISA"; *Journal of Immunological Methods*; 116 (1989) 181–187.

Product Brochure; Magic® Lite Sq™.

"Rapid Detection of Antigen–specific Mouse IgE by Enzyme–linked Immunosorbent Assay (ELISA)"; RJ Strouse et al.; J Immunoassay 1991;12(1):113–24.

"An Enzyme–linked Immunosorbent Assay for Cow's Milk Protein–specific IgE Using Biotinylated Antigen. Avoidance of Interference by Specific IgG"; A. Plebani et al.; J Immunol Methods 1986 Jun. 24;90(2):241–6.

"The Use of Acridinium Ester–labelled Streptavidin in Immunoassays"; RC Hart et al.; J Immunol Methods 1987 Jul. 16:101(1):91–6.

"Effect of Surfactants on the Intensity of Chemiluminescence Emission from Acridinium ester labelled proteins"; FJ Bagazgoitia et al.; J Biolumin Chemilumin 1988 Jul.–Sep.;2(3):121–8.

Methods in Enzymology, 184(1990) Everly Conway de Macario et al: "Slide Immunoenzymatic Assay for Human Immunoglobin E", p. 501–p. 507.

Methods in Enzymology, 184(1990) C.J. Strasburger et al: "Two–Site and Competitive Chemiluminescent Immunoassays", p. 481–p. 496.

Jacobsen L., Evaluation of the Magic Lite SQ Specific IgE Assay, Clinical Chemistry, vol. 36, No. 6, p. 1189, 1990.

Bousquet, J., Comparison between RAST and Pharmacia CAP system: A new automated specific IgE assay, J. Allergy Clinical Immunology, vol. 85, No. 6, pp. 1039–1042, 1990.

Kleine–Tebbe, J. Comparison between Magic Lite and CAP system: two automated specific IgE antibody assays, Clinial and Experimental Allergy, vol. 22, pp. 475–484, 1992.

Wilchek, M., The Avidin–Biotin Complex in Bioanalytical Aplications, Analytical Biochemistry, vol. 171, pp. 1–32, 1988.

Wilchek, M., The Avidin–Biotin Complex in Immunology, Immunology Today, vol. 5, No. 2, pp. 39–43, 1984.

TWO-SITE IMMUNOASSAY FOR AN ANTIBODY WITH CHEMILUMINESCENT LABEL AND BIOTIN BOUND LIGAND

This is a continuation application of U.S. Ser. No. 08/436,188 filled on May 10, 1995, now abandoned.

FIELD OF THE INVENTION

The present invention relates to a method of detecting an antibody in a sample using a chemiluminescent labelling compound.

More specifically, the invention relates to the use of a chemiluminescent acridinium ester compound coupled to avidin or streptavidin, and a ligand coupled to biotin in a two-site immunoassay wherein the affinity complex is captured on paramagnetic particles, which makes possible a rapid detection and/or quantification of immunologically active substances, such as antibodies in samples such as biological fluids and tissue samples, milk, food samples, beverages, water or industrial effluents.

BACKGROUND OF THE INVENTION

A method of detecting and quantifying immunoglobulin E-antibodies in serum is disclosed in the brochure "Specific IgE, Magic® Lite SQ™, published by Ciba Corning Diagnostics Corp. and ALK Laboratories in September 1990. In said method a specific allergen covalently bound to paramagnetic particles reacts with the allergen-specific IgE-antibody in a serum or plasma sample. After a first incubation period and washing away unbound non-specific IgE, a chemiluminescent acridinium ester-labelled monoclonal antibody against IgE is added. Following a second incubation period the solid phase bound and labelled antibody is measured in a Magic Lite® Analyzer (Cat. No. 472733 or Cat. No. 472270) which automatically injects reagents, which initiate the chemiluminescent reaction. When using said method only the final step of initiating and measuring the chemiluminescence can be automated. The chemiluminescent acridinium ester labelling compound is described in U.S. Pat. No. 4,745,181.

U.S. Pat. No. 4,946,958 discloses a chemiluminescent acridinium ester linked to an N-succinimidyl moiety which can be further linked to a protein or polypeptide to provide an immunologically reactive luminescent reagent. Said reagent can be used in an immuno-assay, which may involve the simultaneous binding of a solid phase antibody, an antigen molecule and a labelled anti-antibody, separation and washing of the solid phase and quantifying the luminescence of the solid phase.

Strasburger et al. discloses in Methods in Enzymology, 184(1990), pp 481–496 the use of a two-site chemiluminescent immuno-assay, wherein hGH and hCG hormones are captured by antibodies immobilized on microtiter plates and labelled with a chemiluminescent agent coupled to avidin through a biotin labelled second antibody. Antigenic analytes, such as protein hormones, may be assayed directly from serum samples and compared to standard curves. The concentration of immunoglobulins, such as IgE, is, however, extremely patient dependent and an assay of a specific IgE must be compared with the individual patient level of total IgE and therefore requires an assay having a greater dynamic range than is obtainable in the assay disclosed by Strasburger et al.

EP-A-0 425 217 discloses a hybridization assay wherein a chemiluminescent complex is formed comprising a nucleic acid hybridized with a first labelled nucleotide probe coupled to paramagnetic particles and a second nucleotide probe labelled with biotin and coupled to an avidin-acridinium ester. However, the person skilled in the art confronted with the problem of providing a fully automated method of detecting antibodies will search for a method which can be carried out in one reaction container and preferably under ambient reaction conditions. The assay represented here is fundamentally different as it employs detection of specific nucleotide sequences, which are not antigens towards which specific antibodies can be raised. Moreover, it is necessary in said assay to use elevated temperatures for the hybridization reaction and a hapten-oligonucleotide probe which is not necessary nor desirable in the immuno-assays.

Until now immuno-assays for the quantification of immunologically active molecules, such as immunoglobulins (e.g. specific immunoglobulin-E), in biological fluids, such as serum, have been manual, e.g. the Enzyme Linked Immuno Sorbent Assay (ELISA), or semi-automatical. And the typical duration of a semi-automatical immunoassay, such as the Magic® Lite SQ™ specific IgE assay referred to above, is approximately two hours.

Moreover, commercial specific IgE assays (CAP,RAST, supplied by Pharmacia, Uppsala) and the Magic® Lite SQ™ specific IgE assay use a total-IgE (i.e. the total amount of antibodies present in the immunoglobulin class of IgE including all immunoglobulin subclasses) reference assay having a non-identical protocol resulting in unprecise data. Only assays using the same catching and detection procedures are directly comparable. For example all specific IgE close response curves must be parallel with total IgE response curves. The reason is that the required dynamic range for a specific (or total?) IgE assay is 2 decades and the required dynamic range for a total IgE assay is from 2 to 7 decades, and the existing immuno-assays do not allow concentration measurements over the entire range. Thus, until now it has been necessary to use different protocols for the specific and total immunoglobulin assays having different reagents.

Because of the increasing interest in safe laboratory procedures there is a need for a fully automated method of detecting substances, such as antibodies, in biological fluids, such as human serum, plasma, blood, milk, urine or saliva, which method should provide a minimized risk of contact with hazardous fluids. Also, the increasing use of laboratory tests in diagnostics calls for methods of short duration, preferably only a few minutes.

It is therefore an object of this invention to provide a method of detecting an antibody in a sample, which method is safe, rapid, and fully automatable.

SUMMARY OF THE INVENTION

This object is achieved by one method according to the invention which method comprises in:

a) mixing a ligand antigen, antibody, or hapten bound to biotin or a functional derivative thereof; an antibody directed against the antibody to be detected bound to paramagnetic particles; and a chemiluminescent acridinium compound bound to avidin, streptavidin or a functional derivative thereof with the sample to form a solid phase bound complex, b) magnetically separating the solid phase from the liquid phase, c) initiating the chemiluminescent reaction, and analyzing the separated solid phase for the presence of chemiluminescent complex, wherein the presence of chemiluminescence is an indication of the presence of said antibody in said sample.

BRIEF DESCRIPTION OF THE DRAWINGS

The following drawings are for illustrative purposes only and are not intended to limit the invention as encompassed by the claims forming part of the application.

DETAILED DESCRIPTION OF THE INVENTION

Although the method according to the invention can be carried out by the above defined steps (a), (b) and (c) it is preferred to add the labelling compound in a separate step, and the method is preferably carried out according to the following steps:

i) mixing the ligand antigen, antibody, or hapten bound to biotin or a functional derivative thereof with the samole and the antibody directed against the antibody to be detected bound to paramagnetic particles to form a first solid phase complex, ii) adding a chemiluminescent acridinium compound covalently bound to avidin, streptavidin or a functional derivative thereof to form a second solid phase complex, iii) magnetically separating the solid phase from the liquid phase;

iv) initiating the chemiluminescent reaction, and analyzing the separated solid phase for the presence of the chemiluminescent complex.

A particular object of the invention is to provide a fully automatable immuno-assay for the quantification of specific antibodies, such as immunoglobulins, wherein a truly parallel reference immunoassay using an identical protocol is used as the reference.

The object of quantifying specific antibodies using a truly parallel reference immuno-assay is achieved by a method of measuring the concentration and/or the relative contents of a specific antibody in a liquid sample, wherein the measured light emission of a separated solid phase comprising a captured specific antibody coupled to a chemiluminescent label is compared with the measured light emission obtained in a parallel reference immuno-assay wherein the total contents of the class of antibodies in the sample to which said specific antibody belongs is measured, said method comprising the steps of a) mixing a ligand antigen or hapten towards which the specific antibody to be measured is directly bound to biotin or a functional derivative thereof; an antibody directed against the constant portion of the antibody to be measured bound to paramagnetic particles; and a chemiluminescent acridinium compound bound to avidin, streptavidin or a functional derivative thereof with the sample to form a first solid phase complex, b) magnetically separating said first solid phase from the liquid phase, c) initiating a chemiluminescent reaction and measuring the light emission of the separated first solid phase, d) mixing a ligand antibody directed against the class of antibodies to be measured bound to biotin or a functional derivative thereof; an antibody directed against the constant portion of the class of antibodies to be measured bound to paramagnetic particles; and a chemiluminescent acridinium compound bound to avidin, streptavidin or a functional derivative thereof wherein the term "total" shall mean the entire amount of the designated class of immunoglobulins (e.g. IgA and subclasses thereof), with the sample to form a second solid phase complex, e) magnetically separating said second solid phase from the liquid phase, f) initiating the chemiluminescence reaction and measuring the light emission of the separated second solid phase, and g) comparing the light emission of the separated first solid phase with that of the separated second solid phase.

In a preferred embodiment of the method described above step a) is performed by (i) mixing the ligand antigen or hapten bound to biotin or a functional derivative thereof with the sample and the antibody bound to paramagnetic particles to form a solid phase complex, and (ii) adding the chemiluminescent acridinium compound bound to avidin, streptavidin or a functional derivative thereof to form said first solid phase complex, and step d) is performed by (i) mixing the ligand antibody bound to biotin or a functional derivative thereof with the sample and the antibody bound to paramagnetic particles to form a solid phase complex and (ii) adding the chemiluminescent acridinium compound covalently bound to avidin, streptavidin or a functional derivative thereof to form said second solid phase complex.

The specific antibody to be measured in the sample is preferably a specific immunoglobulin selected from the group consisting of IgA, IgD, IgE, IgG, IgM, and subclasses thereof, and the ligand antigen, antibody, or hapten directed against the variable portion of said antibody is an allergen, and the class of antibodies is preferably a class of immunoglobulins selected from the group consisting of total IgA, total Ig, total IgE, total IgG, total IgM, and subclasses thereof, and the ligand antigen, antibody or hapten is an antibody directed against said class of immunoglobulins.

More preferably the specific immunoglobulin is a specific IgE, and the class of antibodies is total IgE.

The antibody directed against the antibody to be measured bound to paramagnetic particles is preferably selected from the group consisting of polyclonal antibodies, monoclonal antibodies including recombinant antibodies, fragmented antibodies, preferably a monoclonal mouse anti-immunoglobulin.

The advantages of the invention are:

All reagents can be mixed simultaneously in one reaction container, which minimizes the risk of contamination, errors and operation steps, reduces significantly the duration of the immuno-assay, and greatly facilitates automation of the process and precision is improved, cf. example 6;

Quantification of specific antibodies in, e.g. a serum sample, can be performed with reference to a truly parallel total antibody assay using an identical protocol, cf. example 3;

The obtained greater capacity and sensitivity facilitates that even very low concentrations of immunoglobulins and low concentrations of specific immunoglobulins can be detected, cf. examples 1, 2 and 7.

A preferred embodiment of the invention is an immuno-assay for the detection of antibodies, such as specific immunoglobulins (IgA, IgE, IgG, IgM and subclasses thereof) in a sample, such as serum or saliva.

Particularly, the invention can be used in an assay for the detection and quantification of specific IgE in a sample. When the sample is liquid, e.g. serum or plasma, it can be added directly to a reaction container comprising preferably a monoclonal mouse anti-IgE antibody bound to suspended paramagnetic particles and a specific allergen (ligand) bound to biotin in an aqueous medium. The biotin is preferably biotin amidocaproate N-hydroxysuccinimide ester (Sigma Catalog No. B2643) When the sample is non-liquid, e.g. a tissue sample, it is preferably homogenized and suspended in an aqueous liquid. A simultaneous reaction between specific IgE in the sample, allergen and monoclonal anti-IgE antibody in the aqueous medium results in the formation of a conjugate. A chemiluminescent la-belling compound, preferably an acridinium ester coupled to streptavidin (Sigma Catalog No. S4762) (avidin-DMAE) is added to the reaction container and a binding reaction between avidin-DMAE and biotin bound to the conjugate and unconjugated allergen-bound biotin takes place. The conjugate bound label is separated from the unbound DMAE-labelled antibody by magnetically separating the reaction mixture and decanting the supernatant. The chemiluminescence of the separated conjugate is measured as described in Pazzagli, M. et al. (eds.). Studies and applications in "Biology & Medicine", Journal of Bioluminescence and Chemiluminescence 4(1), 1–646, 1989.

As a reference, a truly parallel total-IgE immuno-assay differing only in that a preferably polyclonal anti-IgE antibody bound to biotin is used as the ligand is performed simultaneously.

Figure 1:
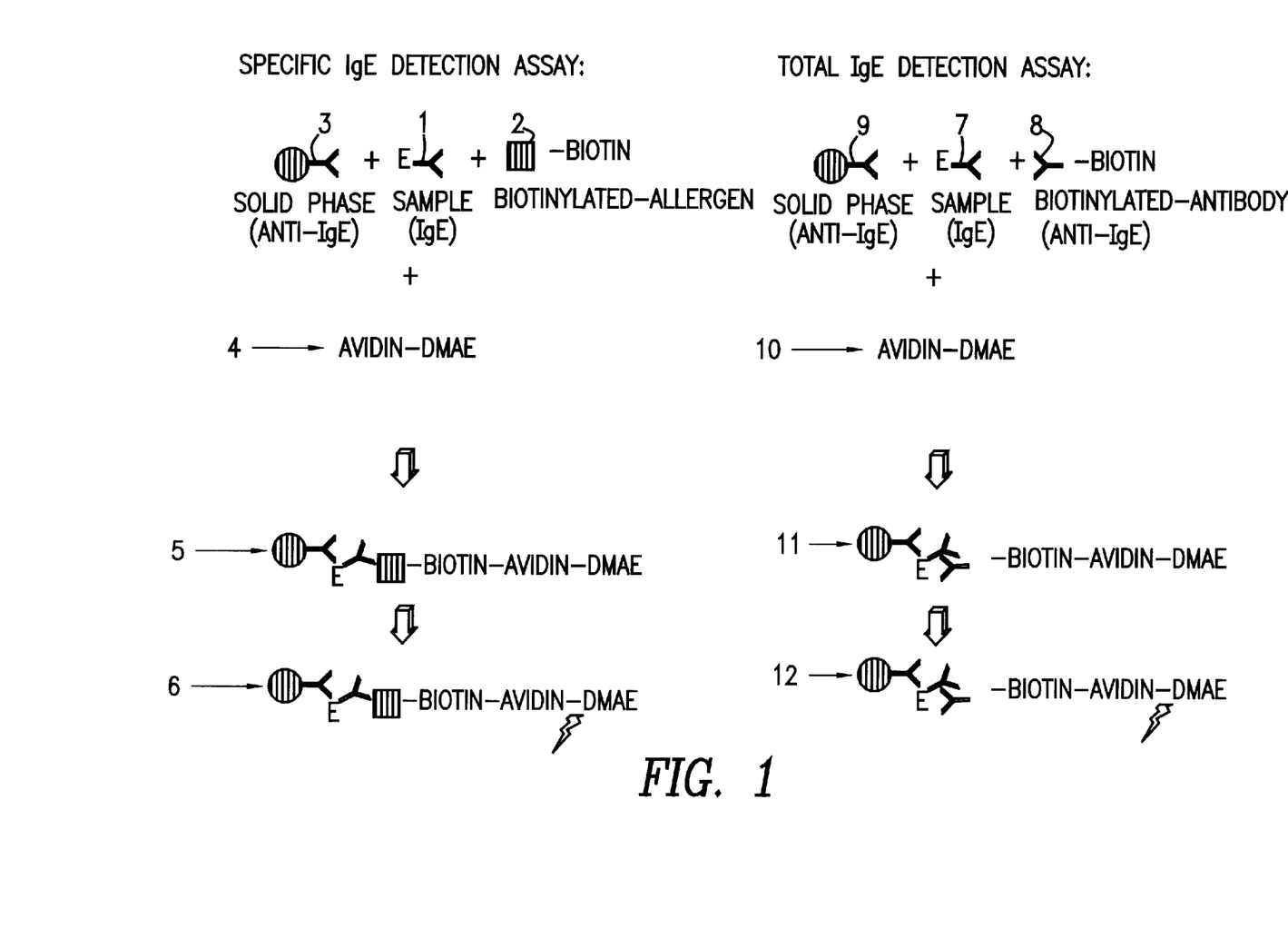
FIG. 1 is a diagrammatic view of a specific IgE assay according to the present invention.

FIG. 1 is a diagrammatic representation of a specific IgE assay according to the invention and comprising a parallel total IgE reference assay. In the FIG. 1 reference numeral (1) represents the specific IgE-antibody to be detected, (2) is a specific allergen bound to biotin, (3) is a monoclonal mouse anti-IgE bound to paramagnetic particles, (4) is an avidin-acridinium ester and (5) represents the solid phase labelled complex formed between (1), (2), (3) and (4) and includes optional incubation, separation and optional washing steps, and (6) represents a final step of initiating the chemiluminescent reaction and measuring the light emission.

In the total IgE reference assay in FIG. 1 (7) represents IgE (WHO 75/502 IU/ml), (8) is polyclonal anti-IgE bound to biotin, (9) is monoclonal mouse anti-IgE bound to suspended paramagnetic particles, (10) is an avidin-acridinium ester and (11) represents the solid phase labelled complex formed between (7), (8), (9) and (10) and includes optional incubation, separation and optional washing steps, and (12) is the final step of initiating the chemiluminescent reaction and measuring the light emission.

More particularly, the immuno-assay using the method of the invention can be performed in ACS:180 fully automatic analyzer produced by Ciba Corning Diagnostics Corp., Medfield, Mass., U.S.A.

In one preferred embodiment of the invention the immunologically active substance to be detected is an antibody, e.g. against penicillin or derivatives thereof, such as benzylpenicillin, penicilloyl, etc., and the ligand bound to biotin is a hapten, such as penicillin or derivatives thereof.

Definitions

In the methods of the invention the antibody to be detected is a specific immunoglobulin, preferably a specific IgA, IgD, IgE, IgG, IgM, and subclasses thereof, and more preferably a specific IgE, or a class of antibodies, such as immunoglobulins, preferably selected from the group consisting of total IgA, total Igd, total IgE, total IgG, total IgM and isotypes thereof, most prefer ably total IgE.

By sample is meant any liquid or liquefied sample, including solutions, emulsions, dispersions and suspensions.

The ligand antigen, antibody or hapten bound to biotin can be any immunologically active substance, such as an allergen, antibodies, such as polyclonal antibodies, monoclonal antibodies including recombinant antibodies or fragmented antibodies, preferably an allergen and/or a polyclonal anti-immunoglobulin, such as goat anti-human polyclonal serum supplied by Ventrex Laboratories, Inc., Portland, Me., Catalog No. 77660. In the reference immuno-assay said antibody is preferably directed against the constant portion of the class of antibodies to be measured, i.e. an antibody directed against the IgE-antibodies.

By biological fluid is meant any clinical sample, such as blood, plasma, serum, urine or saliva, which also includes any biological fluid which is excreted, secreted or transported internally in an organism.

By paramagnetic particles (PMP) is meant particles which can be dispersed or suspended in a liquid medium. The examples employ BioMag particles (iron oxide particles coated with amine terminated groups) sold by advanced Magnetics Inc. , Cambridge, Mass. The antibodies coupled to PMP are preferably directed against the constant portion of the antibodies to be detected or measured and may be polyclonal or monoclonal antibodies including recombinant or fragmented antibodies, preferably a monoclonal antibody, MAb A 5697-1A3(920325) supplied by BioInvent International AB, Lund, Sweden.

The chemiluminescent acridinium compound is preferably N-hydroxy-succinimide dimethylacridinium ester covalently bound to avidin or streptavidin (avidin-DMAE). Avidin and DMAE are coupled according to the methods of Weeks et al., Clin. Chem. 29/8, 1474–1479 (1983). Other luminescent labelling compounds that can be bound to avidin or streptavidin may be used in the method of the invention. E.g. luminol, lucigenin or lophine.

Preparation of Biotinylated Antibodies

Biotinylated Anti-IgE and Phleum Pratense:

Goat anti-human polyclonal serum (Ventrex Laboratories, Inc. MA, USA) is purified by affinity chromatography on a CNBr-activated sepharose 4B (Pharmacia, Uppsala, Sweden) with myeloma IgE (OEM concepts, USA) as a ligand. The anti-IgE is biotinylated with the ratio mol biotin: mol anti-IgE=41:1.

9 $\mu$l of Biotin (Biotin amidocaproate N-hydroxysuccinimide ester (Sigma) 25 mg/ml in Dimethylformamide (Merck) is added to 0.4 ml of anti-IgE 4.5 mg/ml in 0.1 M $NaHCO_3$ (Merck). The reagents are incubated in an "end over end" mixer for 2 hours at 25° C. 0.9 ml lysin (Sigma) solution 20 mg/ml NaHCO$_3$ is added. The solution is filtered and the biotinylated antibody is purified by size chromatography on superdex 75 Hiload 16/60 (Pharmacia, Uppsala, Sweden). The pooled fractions are diluted in phosphate buffered saline PBS, pH 7.2, containing 0.1% human serum albumin (Sigma) 0.1% NaN$_3$ (Sigma).

The Phleum pratense extract, (ALK Laboratories A/S, Hørsholm, Denmark) is biotinylated in the molar ratio of 10:1, 0.65 ml of biotin 10 mg/ml is added to 0.43 ml of 10 mg/ml Phleum pratense in 0.1 M NaHCO$_3$. The reagents are incubated for 2 hours at 25° C. in an "end over end" mixer, after the incubation 40 µl lysin (Sigma) solution 50 mg/ml is added. The solution is filtered and the biotinylated antibody is purified from excess of biotin by size exclusion chromatography on superdex 75 Hiload 16/60 (Pharmacia). The fractions containing the allergens are pooled. The biotinylated Phleum pratense is diluted with PBS pH 7.2, containing 0.1% human serum albumin (Sigma) and 0.1% NaN$_3$ (Sigma).

Preparation of Streptavidin-acridinium Ester Label

Streptavidin was conjugated with DMAE-NHS, [2',6'-dimethyl-4'-(N-succinimidyloxycarbonyl)phenyl-10-methylacridinium-9-carboxylate methosulphate] using the methods of Weeks et al., Clin.Chem. 29/8, 1474–1479 (1983).

Preparation of Streptavidin-acridinium Ester Label:

0.96 mg N-hydroxysuccinimide dimethylacridinium ester DMAE (Ciba Corning Diagnostics Corp., Medfield, Mass., USA) is diluted in 1.92 ml Dimethylformamide. 250 µl of this solution is pipetted to 2.5 ml 1 mg/ml streptavidin (Sigma) in 0.1 M sodium dihydrogenphosphate, 0.15 M NaCl pH 8.15.

The air above the solution in the vial is exchanged with nitrogen, (AGA). The reagents are incubated for 30 min at 25° C. under stirring, after incubation 2250 µl 10 mg/ml lysin 0.1 M sodium dihydrogenphosphate (Merck), 0.15 M NaCl is (Merck) pH 8.15 is added. To remove unbound DMAE the solution is loaded on a PD-10 column (Pharmacia, Uppsala, Sweden). The eluate is collected and purified by ultrafiltration using a cellulose Minitan-S filter sheet 10.000 NMWL (Millipore). The filtration is performed with 1.5 l phosphate buffered saline, PBS pH 7.2. The retentate (retanate) is concentrated to 25 ml and 25 ml PBS pH 7.2 containing 0.5% HSA (Sigma) and 0.1% NaN$_3$ (Sigma) is added.

The invention will be described in detail in the following examples.

Immobilisation of Antibody to Paramagnetic Particles 6.5 g paramagnetics particles (Ciba Corning Diagnostics Corp., MA, USA) are washed in 650 ml methanol (Merck) 3 times using magnetic separation. A wash with 650 ml 0.01 M acetate buffer pH 5.5 is performed twice. The particles are activated in 6.25% glutaraldehyde (Merck), 0.01 M acetate buffer pH 5.5 for 3 hours at 25° C. The particles are washed 3 times in 650 ml 0.01 M acetate buffer pH 5.5. The particles are coupled with 1083 mg monoclonal anti-IgE antibody (ALK Laboratories, Hørsholm, Denmark) specific against the IgE Fc domain, for 24 hours at 25° C. The particles are washed twice in 0.01 M acetate buffer pH 5.5. Blocking of excess of active groups is performed with 200 ml 10% IgE stripped serum (ALK Laboratories, Hørsholm, Denmark) for 24 hours at 25° C. The particles are washed in 650 ml 0.01 M phosphate buffer (Merck) followed by 3 washes in 650 ml 1 M NaCl (Merck). The particles are washed 3 times in 0.01 M phosphate buffer. The particles are resuspended in 650 ml PBS pH 7.2, 0.1% w/v bovine serum albumine (Sigma), 0.001% bovine gamma globulin (Sigma) and heat treated for 18 hours at 50° C. The partides are washed 3 times in 650 ml PBS pH 7.2, 0.1% w/v bovine serum albumine (Sigma), 0.001% bovine gamma globulin (Sigma). The particles are heat treated for 7 days at 37° C. The particles are washed in 0.01 M phosphate buffer twice. The particles are diluted to 0.5 g per 1 in PBS pH 7.2, 0.5% human serum albumine (Sigma).

EXAMPLE 1

Detection and Quantification of Antigen (total IgE)

Determination of total IgE antibodies, according to the invention, was conducted on Ciba Corning ACS:180 Benchtop Immunoassay analyzer described in Clinical Chemistry, 36/9, 1598–1602 (1990), using the following protocol:

50 µl of sample and 50 µl biotinylated anti-IgE are dispensed by the sample probe into the cuvette. The cuvette reaches the first reagent probe R1, where 100 µl paramagnetic particles with immobilised monoclonal anti-IgE antibody (ALK Laboratories A/S, Hørsholm, Denmark) specific against the IgE Fc domain are dispensed together with 200 µl of streptavidin-acridinium ester label (ALK Laboratories A/S, Hørsholm, Denmark). The cuvette moves down the track to the magnets and wash station. Washing with 750 µl deionized water is performed twice. After completion of the wash cycle the particles are resuspended in 300 µl 0.5 g/l H$_2$O$_2$ in 0.1 M HNO$_3$. The cuvette enters the luminometer chamber and in front of the photomultiplier 300 µl 25 mM NaOH solution is added and the photons of light emitted are measured and quantitated and expressed as relative light units (RLU). The amount of RLU is directly proportional to the amount of the IgE in the sample. The time from sample dispension to first result is 15 min and a new result follows every 20 second. Results were expressed as RLU experiment/RLU background, where RLU background was the chemiluminescent reaction observed in the absence of total IgE.

Figure 2:
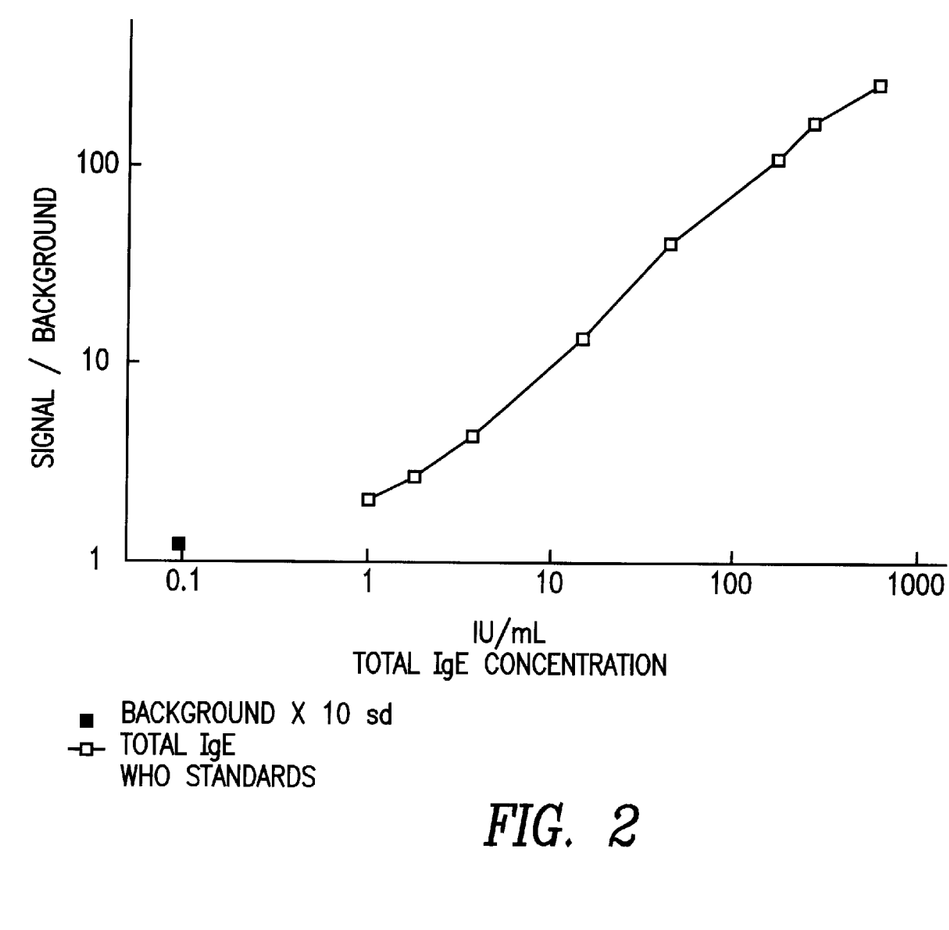
FIG. 2 is a graph showing the detection of Total IgE in accordance with Example 1.

Nine Total IgE standards, calibrated in Magic Lite Total IgE Kit (ALK Laboratories A/S, Hørsholm, Denmark) against WHO 2nd IRP no 75/502 for human serum IgE, were assayed using the protocol described above and it is shown that 0.1 IU/ml of total serum IgE could be detected (as determined by background×10 standard deviations), see FIG. 2.

EXAMPLE 2

Detection and Quantification of Specific Antibody (Specific IqE)

Determination of Phleum pratense specific IgE antibodies (timothy grass specific IgE, according to the invention, was conducted on Ciba Corning ACS:180 Benchtop Immunoassay analyzer described in Clinical Chemistry, 36/9, 1598–1602 (1990), using the following protocol:

50 µl of sample and 50 µl biotinylated Phleum pratense are dispensed by the sample probe into the cuvette. The cuvette reaches the first reagent probe R1, where 100 µl paramagnetic particles with immobilised monoclonal anti-IgE antibody (ALK Laboratories A/S, Hørsholm, Denmark) specific against the IgE Fc domain are dispensed together with 200 µl of streptavidin-acridinium ester label (ALK Laboratories A/S, Hørsholm, Denmark). The cuvette moves down the track to the magnets and wash station. Wash with 750 µl deionized water is performed twice. After completion of the wash cycle the particles are resuspended in 300 µl 0.5 g/l H$_2$O$_2$ in 0.1 M HNO$_3$. The cuvette enters the luminometer chamber and in front of the photomultiplier 300 µl 25 mM NaOH solution is added and the photons of light emitted are measured and quantitated and expressed as relative light units (RLU). The amount of RLU is directly proportional to the amount of the IgE in the sample. The time from sample dispension to first result is 15 min and a new result follows every 20 second. Results were expressed as RLU experiment/RLU background, where RLU background was the chemiluminescent reaction observed in the absence of total IgE.

Figure 3:
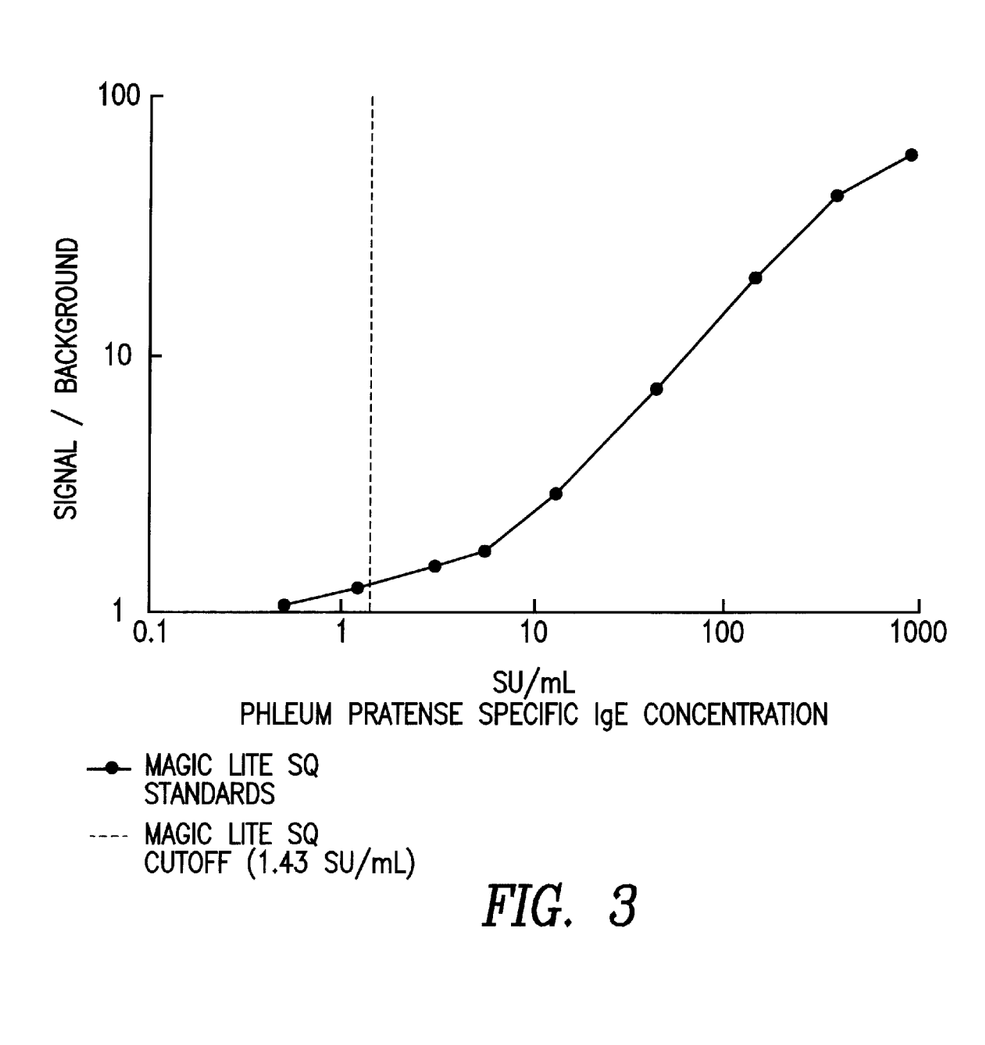
FIG. 3 is a graph showing the detection of phleum pratense specific IgE in accordance with Example 2.

Ten Phleum pratense specific IgE standards, calibrated in Magic Lite SQ Specific IgE Kit (ALK Laboratories A/S, Hørsholm, Denmark) against clinically characterised Phleum pratense allergic patients samples and expressed as SU/ml (Standardised Units), were assayed using the protocol described above and it is shown that between 1.43 and 800 SU/ml of Phleum pratense specific IgE can be measured as in Magic Lite SQ Specific IgE assay, see FIG. 3.

EXAMPLE 3
Quantification of Specific IgE Against WHO Total IgE Reference

Quantification of specific IgE antibodies in serum samples were performed with reference to total IgE antibody or specific IgE antibody using the identical assay protocols as described in example one and two, respectively.

Thirty five patient samples were assayed for Phleum pratense specific IgE along with 10 Phleum pratense specific IgE standards, calibrated in Magic Lite SQ Specific IgE Kit (ALK Laboratories A/S, Hørsholm, Denmark) against clinically characterised Phleum pratense allergic patient samples and expressed as SU/ml (protocol described in example 2).

Nine standards of IgE WHO 2nd IRP No. 75/502 (National biological standard board) were assayed in the same run against total IgE (protocol described in example 1).

Figure 4:
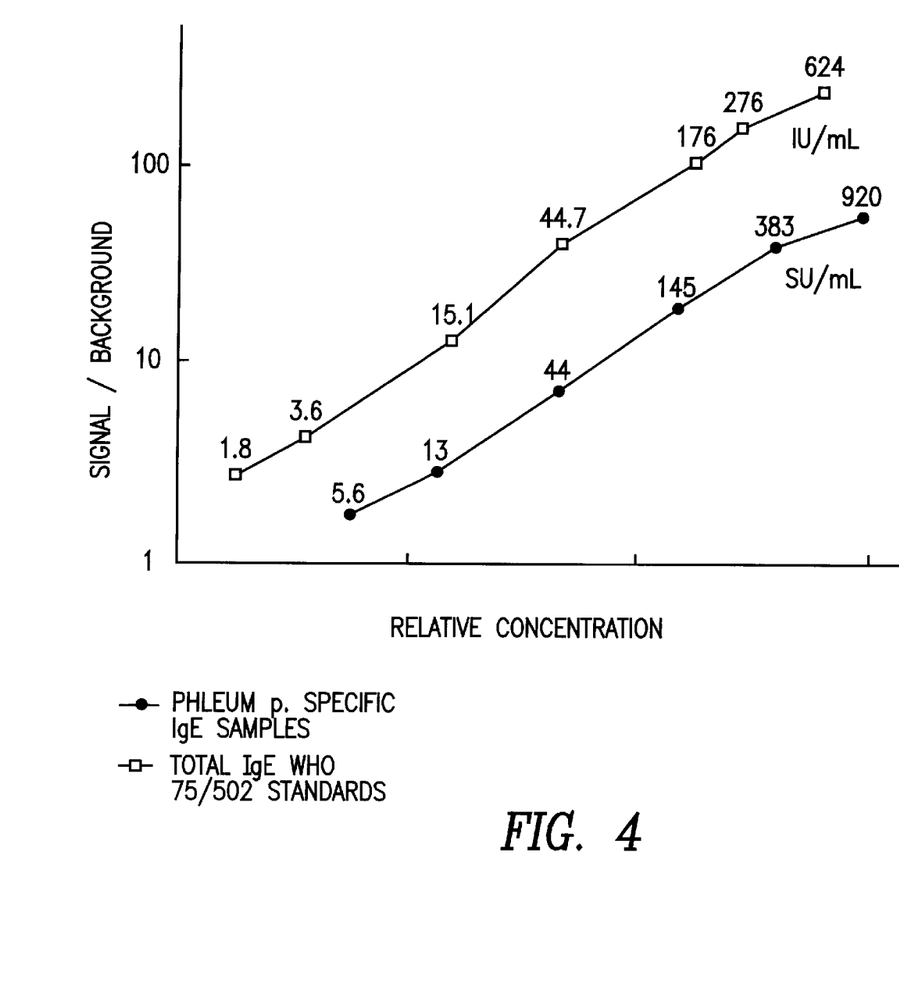
FIG. 4 is a graph showing a comparison of two dose response curves of total IgE assay and phleum pratense specific IgE assay.

FIG. 4 provides a comparison of the two dose response curves of total IgE assay and Phleum pratense specific IgE assay respectively. Parallel line test showed no significant difference in slopes between the two dose response curves, indicating that specific IgE in patient samples could be calibrated against the WHO Total IgE standard and expressed in IU/ml.

Figure 5:
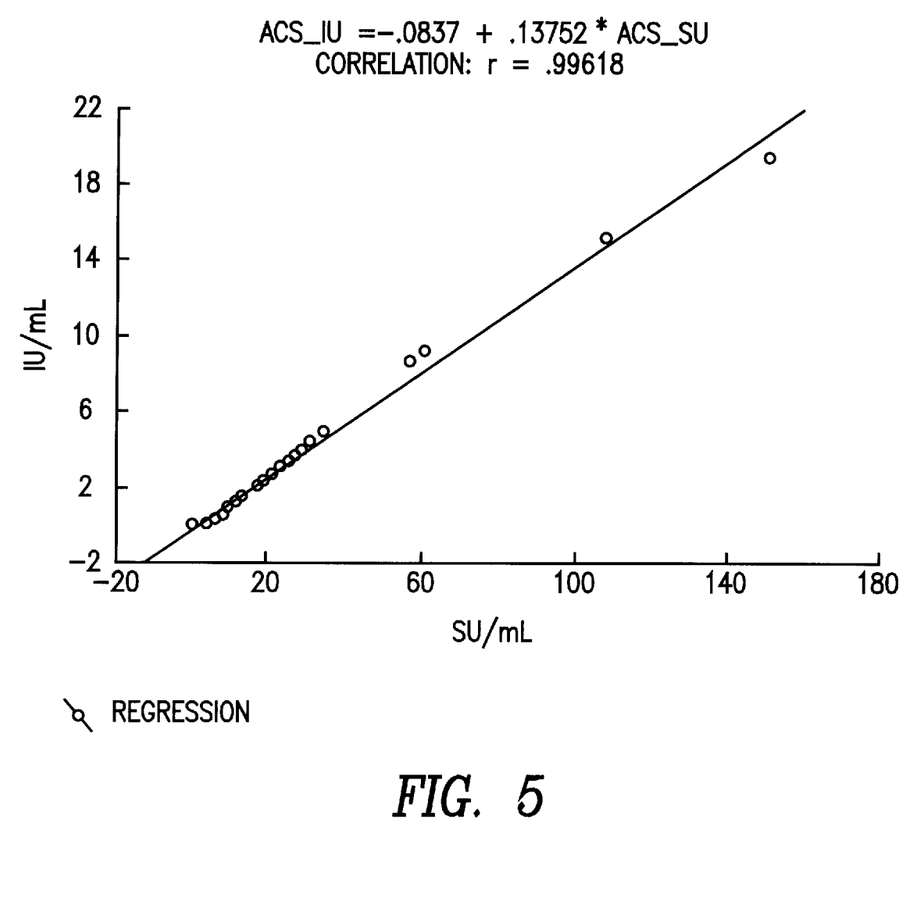
FIG. 5 is a graph showing a comparison of patient samples calibrated against WHO total IgE standards and phleum pratense specific IgE standards.

FIG. 5 provides a comparison of results from the 35 patient samples calibrated against WHO Total IgE standards (expressed in IU/ml) or Phleum pratense specific IgE standards (expressed in SU/ml) and it shows very good correlation between the two units.

The concentration (dose) of the unknown sample was calculated using a cubic-free spline interpolation after a log vs. log transformation of signal/background and concentration (dose), respectively.

It was calculated from the linear regression line that one SU (Standardised Unit) corresponds to 0.14 International Unit (IU).

In conclusion allergen specific IgE can be measured using the embodiment of the present invention and calibrated directly from the total IgE assay of a WHO IgE calibrated standard curve.

EXAMPLE 4
Total IgE Method Comparison

Thirtythree patients samples were measured for total serum IgE in the Magic Lite Total IgE kit (ALK Laboratories A/S, Hørsholm, Denmark). The assay was performed according to the manufacturer's instruction. The same samples were measured for total serum IgE on the ACS:180 according to the protocol described in example 1.

Figure 6:
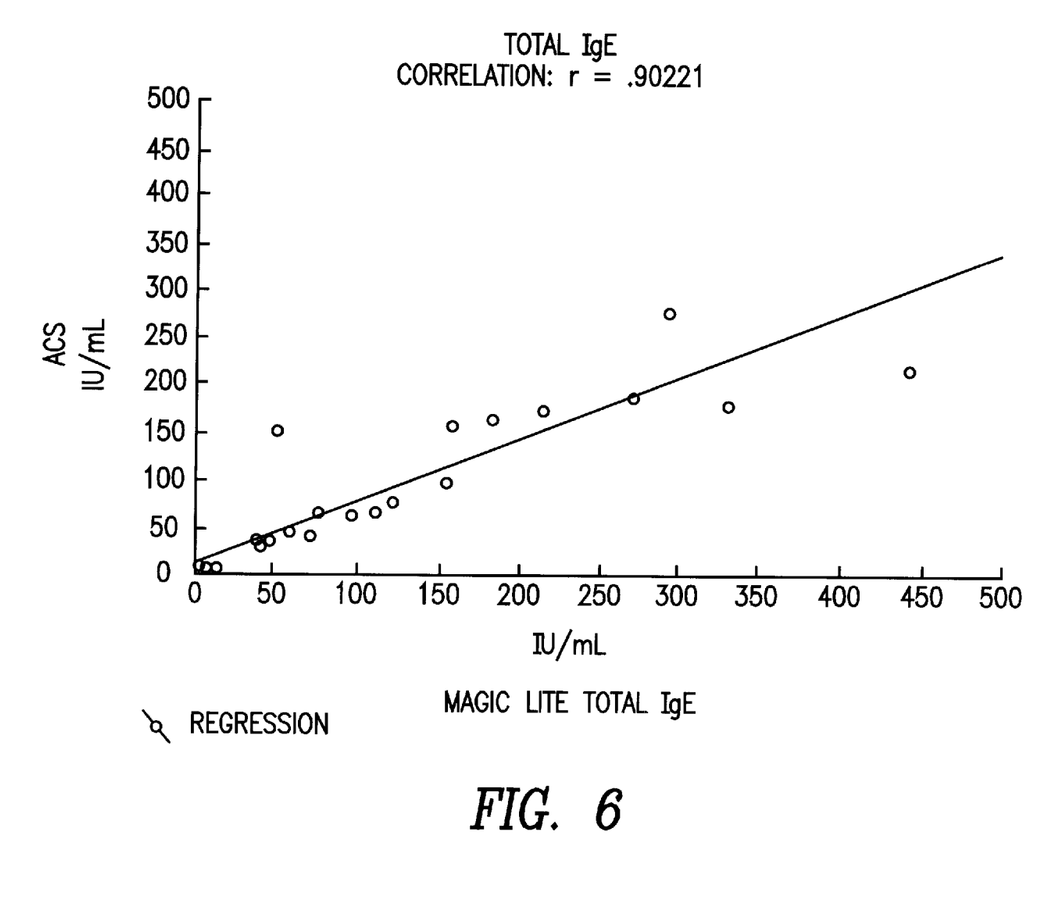
FIG. 6 is a graph showing a comparison of measured total serum IgE of Example 4.

FIG. 6 provides a scatterplot for the method comparison for measuring total serum IgE. A correlation with r=0.90 was found.

EXAMPLE 5
Specific IgE Method Comparison

Thirty five patients samples were measured for Phleum pratense specific IgE in the Magic Lite SQ Specific IgE kit (ALK Laboratories A/S, Hørsholm, Denmark). The assay was performed according to the manufacturer's instruction. The same samples were measured for Phleum pratense specific IgE on the ACS:180 according to the protocol described in example 2.

Figure 7:
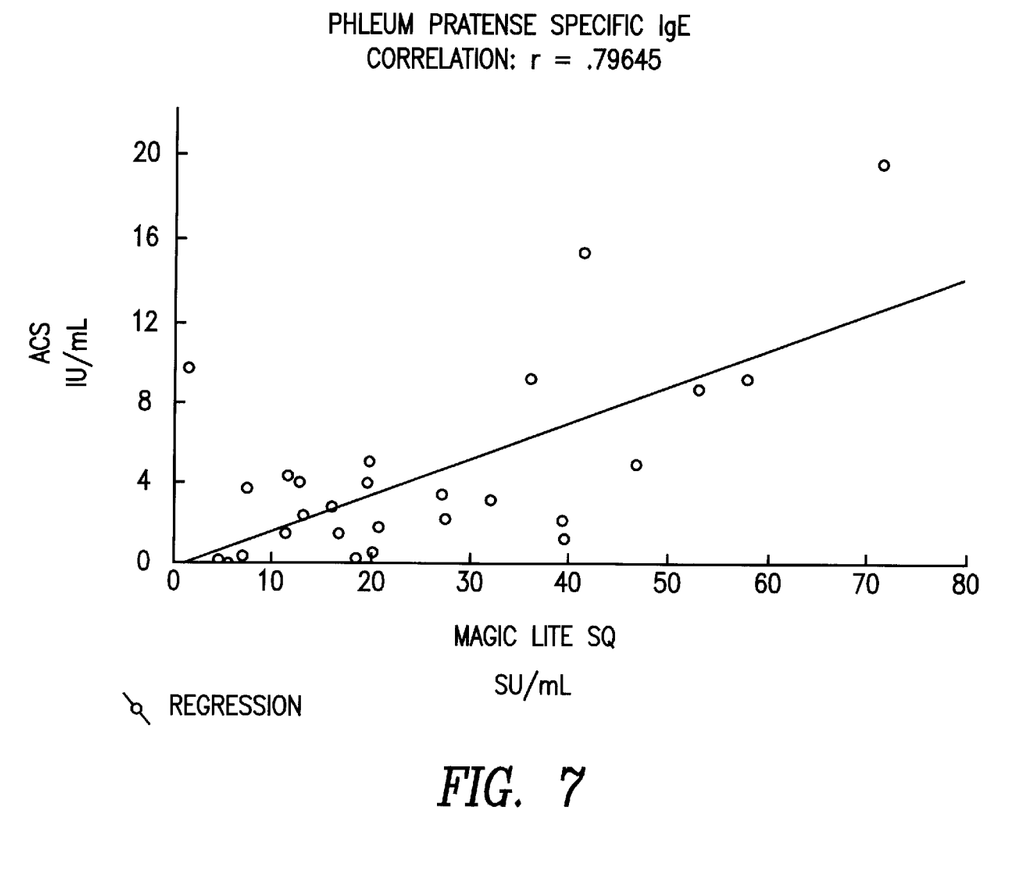
FIG. 7 is a graph showing a comparison of measured phleum pratense specific IgE as in Example 5.

FIG. 7 provides a scatterplot for the method comparison for measuring Phleum pratense specific IgE. A correlation with r=0.80 was found.

EXAMPLE 6
Comparison of Assay Precision

The within-run imprecision for ACS total IgE using the protocol described in example 1, was compared to that of Magic Lite Total IgE. Patient samples were run in replicates of three in the assays described in example 4. The pooled within-run coefficient of variation (CVpwr) was calculated according to Krouwer and Rabinowitz, Clinical Chemistry, 30, 290 (1984). The following results were obtained:

|          | Magic Lite | ACS  |
|----------|------------|------|
| % CV pwr | 4.69       | 2.75 |
| Min % CV | 0.80       | 0.70 |
| Max % CV | 11.70      | 8.40 |

As seen from the results, automation and minimation of operating steps significantly improves the precision of the analysis (by F-test: F=1.71, p=0.049).

EXAMPLE 7
Comparison of Total and Specific IgE in Patient Samples:

The samples measured for Phleum pratense specific IgE on the ACS:180 according to the protocol described in example 2 and calibrated against total IgE reference (WHO 75/502) as described in example 3, were also analysed for total IgE as described in example 1. The ratio between measured specific IgE and total IgE was calculated on each sample and expressed as % ratio (spec. IU/total IU*100).

The following results were obtained:

| No | Phleum pratense Specific IgE IU/ml | Total IgE IU/ml | % Ratio |
|----|------------------------------------|-----------------|---------|
| 1  | 0.973  | 208.300 | 0.467  |
| 2  | 0.000  | 153.330 | 0.000  |
| 3  | 0.000  | 25.119  | 0.000  |
| 4  | 0.000  | 43.980  | 0.000  |
| 5  | 0.082  | 51.997  | 0.158  |
| 6  | 0.586  | 30.807  | 1.902  |
| 7  | 9.130  | 20.796  | 43.903 |
| 8  | 2.125  | 168.771 | 1.259  |
| 9  | 1.545  | 321.553 | 0.480  |
| 10 | 0.000  | 299.105 | 0.000  |
| 11 | 1.664  | 248.660 | 0.669  |
| 12 | 8.553  | 46.635  | 18.340 |
| 13 | 19.427 | 234.858 | 8.272  |
| 14 | 0.000  | 178.304 | 0.000  |
| 15 | 2.380  | 428.987 | 0.555  |
| 16 | 4.342  | 112.457 | 3.861  |
| 17 | 3.975  | 173.793 | 2.287  |
| 18 | 0.220  | 206.580 | 0.106  |
| 19 | 0.158  | 298.630 | 0.053  |
| 20 | 4.936  | 17.116  | 28.839 |
| 21 | 0.376  | 146.939 | 0.256  |

-continued

| No | Phleum pratense Specific IgE IU/ml | Total IgE IU/ml | % Ratio |
|---|---|---|---|
| 22 | 4.865 | 23.521 | 20.684 |
| 23 | 3.115 | 281.804 | 1.105 |
| 24 | 0.017 | 17.937 | 0.095 |
| 25 | 3.446 | 160.651 | 2.145 |
| 26 | 1.485 | 167.427 | 0.887 |
| 27 | 2.763 | 124.309 | 2.223 |
| 28 | 3.705 | 247.679 | 1.496 |
| 29 | 1.289 | 196.314 | 0.657 |
| 30 | 8.967 | 416.528 | 2.153 |
| 31 | 0.355 | 29.784 | 1.192 |
| 32 | 15.173 | 290.670 | 5.220 |
| 33 | 2.141 | 63.847 | 3.353 |
| 34 | 3.929 | 96.951 | 4.053 |
| 35 | 0.154 | >620 | ND |

Figure 8:
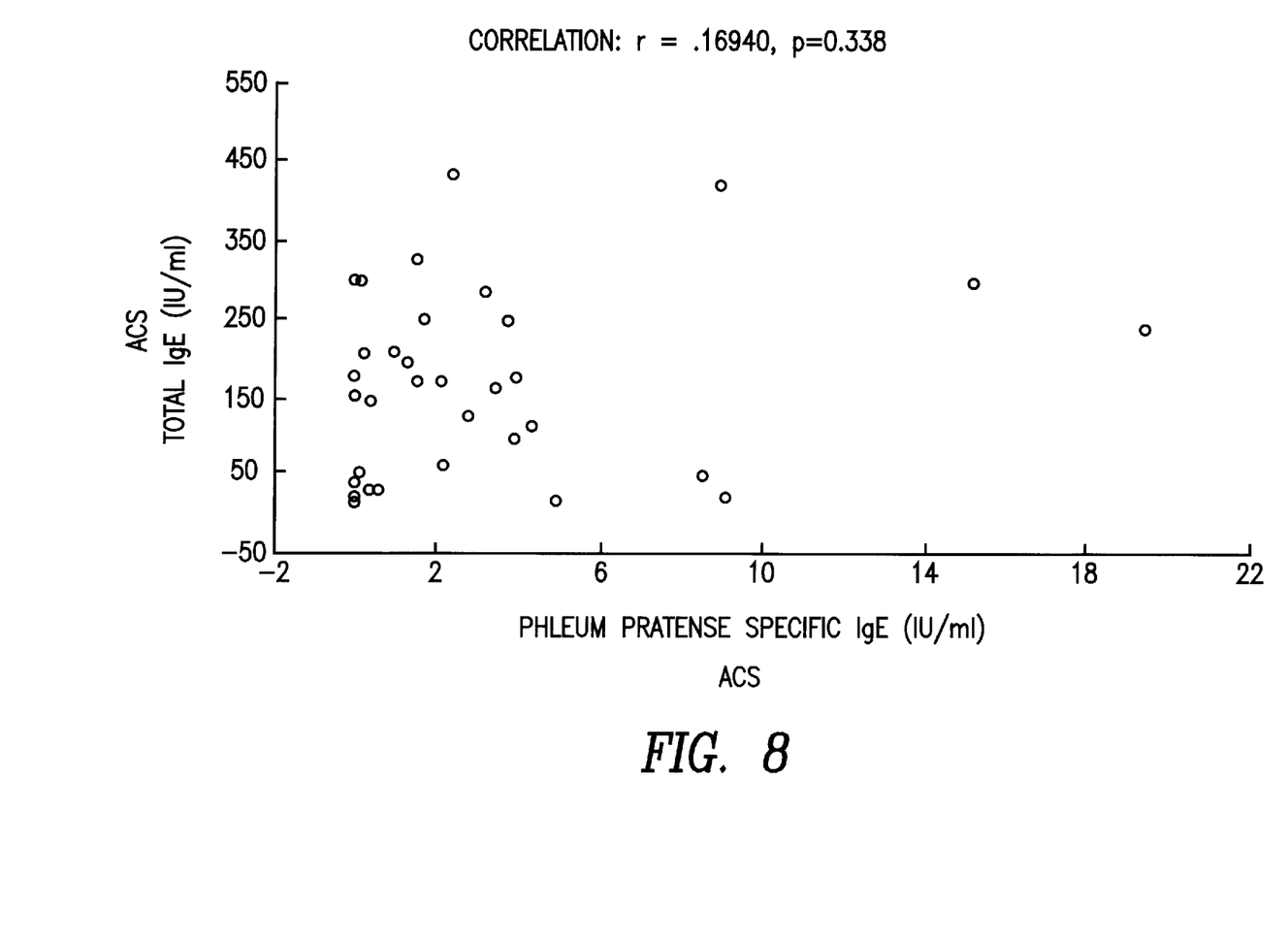
FIG. 8 is a graph showing the correlation between total IgE concentration and phleum pratense specific IgE concentration in accordance with Example 7.

As seen from the results the Phleum pratense specific IgE assay was able to measure as low as 0.05% of Phleum pratense specific IgE out of total IgE. Low relative amounts of Phleum pratense specific IgE indicates that other allergen specificities are present in the samples. Up to 44% of total IgE was found in one patient sample to be specific against Phleum pratense. No correlation was found between total IgE concentration and Phleum pratense specific IgE concentration as seen in FIG. 8.

EXAMPLE 8

Determination of serum total IgA antibodies using paramagnetic particles and avidin-acridinium ester label.

The determination of total IgA antibodies was assayed using the following protocol:

25 μl of patient sample or calibrator was pipetted into a 12×75 mm test tube. To each tube 50 μl of biotinylated polyclonal anti-IgA antibody DAKO E484 (supplied by DAKO, Glostrup, Denmark) in 0.05 M phosphate buffer, pH 7.4, containing 0.1% sodium azide, 0.01% Tween® 20 and 0.1% human serum albumin was added and reacted for 15 minutes at ambient temperature. 400 μl slurry of paramagnetic particles with immobilised polyclonal anti-IgA antibody DAKO A 262, (supplied by DAKO, Glostrup, Denmark) was added to each tube and incubated for 5 minutes. After this second incubation 50 μl of streptavidin-acridinium ester label diluted in the same buffer as described above was added to each tube and incubated for a further 5 minutes at ambient temperature. The paramagnetic particles were washed twice with a 0.2 M phosphate buffer, pH 7.4, containing 0.1% polyoxyethylene sorbitane monolaurate, after separating the magnetic particles from the liquid by a magnetic base separator and vortexing the separated particles with the washing buffer as described above. The contents of the tubes were finally measured in the luminometer, where light emitted at 426 nm, was quantitated and expressed as relative light units (RLUs).

Total IgA standards calibrated against WHO No. 67/86 for human serum IgA DAKO X908 (supplied by DAKO, Glostrup, Denmark) were assayed using the above described protocol.

Standards:

| Concentration (μg/ml) | RLUs |
|---|---|
| 0 | 370937 |
| 0.02 | 417000 |
| 0.23 | 557563 |
| 2.32 | 1252260 |
| 23.2 | 1872357 |

It should be apparent to one having ordinary skill in the art that many variations are possible without departing from the spirit and scope of the invention.

What is claimed is:

1. A method of detecting a detectable antibody in a sample suspected of containing the same comprising:
   a) combining a ligand complex comprising a ligand bound to biotin or a functional derivative thereof; a first antibody complex comprising an antibody having a binding affinity for the detectable antibody bound to paramagnetic particles; and a chemiluminescent complex comprising a chemiluminescent acridinium compound bound to avidin, streptavidin or a functional derivative thereof, with the sample to form a solid phase complex and a liquid phase, said ligand having a binding affinity for the detectable antibody and being selected from the group consisting of an antigen, an antibody and a hapten;
   b) magnetically separating the solid phase complex from the liquid phase;
   c) initiating a chemiluminescent reaction in said separated solid phase complex to form a detectable chemiluminescent complex, and detecting the presence of said detectable chemiluminescent complex, wherein the presence of said detectable chemiluminescence complex is an indication of the presence of said detectable antibody in said sample.

2. The method of claim 1, comprising:
   i) combining the ligand complex with the sample and the first antibody complex to form a first solid phase complex;
   ii) adding said chemiluminescent complex to the first solid phase complex to form a second solid phase complex;
   iii) magnetically separating the second solid phase complex from the liquid phase;
   iv) initiating the chemiluminescent reaction to form said detectable chemiluminescent complex from said second solid phase complex, and detecting the presence of said detectable chemiluminescent complex.

3. A method of claim 2 wherein the detectable antibody is a specific immunoglobulin selected from the group consisting of specific IgA, IgD, IgE, IgG, IgM, and subclasses thereof, and the ligand is a specific allergen.

4. The method of claim 3, wherein the specific immunoglobulin is a specific IgE.

5. The method of claim 1, wherein the detectable antibody is a class of immunoglobulins selected form the group consisting of total IgA, total IgD, total IgE, total IgG, and total IgM, and the ligand is an antibody directed against said class of immunoglobulins.

6. The method of claim 5, wherein the immunoglobulins is total IgE.

7. The method of claim 1 wherein the first antibody complex is selected from the group consisting of polyclonal antibodies, monoclonal antibodies, and fragmented antibodies.

8. The method of claim 7 wherein the monoclonal antibodies are recombinant antibodies.

9. The method of claim 7 wherein the fragmented antibodies are monoclonal mouse anti-immunoglobulin.

10. The method of claim 1, wherein the chemiluminescent complex is N-hydroxysuccinimide dimethylacridinium ester covalently bound to avidin, streptavidin or a functional derivative thereof.

11. A method of measuring at least one of the concentration and relative contents of a detectable antibody in a sample, wherein the measured light emission of a separated solid phase complex comprising a specific antibody coupled to a chemiluminescent label is compared with the measured light emission obtained in a parallel reference immunoassay and wherein the total content of the class of antibodies in the sample to which said detectable antibody belongs is measured, said method comprising:

a) combining a first ligand complex comprising a first ligand selected from the group consisting of an antigen and a hapten bound to biotin or a functional derivative thereof, said ligand having a binding affinity for the detectable antibody; a first antibody complex comprising an antibody directed against a constant portion of the detectable antibody bound to paramagnetic particles, and a chemiluminescent complex comprising a chemiluminescent acridinium compound bound to avidin, streptavidin or a derivative thereof with the sample to form a first solid phase complex and a liquid phase;

b) magnetically separating said first solid phase complex from the liquid phase;

c) initiating a chemiluminescent reaction in said separated solid phase complex to form a first detectable chemiluminescent complex and measuring the light emission of the first detectable chemiluminescent complex;

d) combining a second ligand complex comprising a second ligand selected from the group consisting of antibodies having a binding affinity for said class of antibodies to be measured bound to biotin or a functional derivative thereof; the first antibody complex; and said chemiluminescent complex with the sample to form a second solid phase complex;

e) magnetically separating said second solid phase complex from the liquid phase;

f) initiating a chemiluminescence reaction in said separated second solid phase to form a second detectable chemiluminescent complex and measuring the light emission of the second detectable chemiluminescent complex; and g) comparing the light emission of the first detectable chemiluminescent complex with the light emission of the second detectable chemiluminescent complex.

12. The method according to claim 11, wherein step a) comprises:
i) mixing the first ligand complex with the sample and the first antibody complex to form a first intermediate solid phase complex; and
ii) adding the chemiluminescent complex to the second intermediate solid phase complex to form said second solid phase complex.

13. The method of claim 11, wherein the detectable antibody is a specific immunoglobulin selected from the group consisting of IgA, IgD, IgE, IgG, IgM, and subclasses thereof, and the first ligand includes an allergen, and the class of antibodies to be measured is a class of immunoglobulins selected from the group consisting of total IgA, total IgD, total IgE, total IgG, and total IgM, and the second ligand is an antibody directed against said class of immunoglobulins.

14. The method of claim 13, wherein the specific immunoglobulin is a specific IgE, and the class of antibodies is total IgE.

15. The method of claim 11 wherein the antibody of said first antibody complex is selected from the group consisting of polyclonal antibodies, monoclonal antibodies, and fragmented antibodies.

16. The method of claim 15 where the monoclonal antibodies are recombinant antibodies.

17. The method of claim 15 wherein the fragmented antibodies are monoclonal mouse anti-immunoglobulin.

18. The method of claim 11, wherein the chemiluminescent complex comprises N-hydroxysuccinimide dimethylacridinium ester covalently bound to avidin, streptavidin or a functional derivative thereof.

* * * * *